United States Patent
Cho (10) Patent No.: US 11,432,827 B2
(45) Date of Patent: Sep. 6, 2022

(54) GUIDE MODULE HAVING OBLIQUE INSTALLATION PINS

(71) Applicant: CUSTOMEDI CO., LTD., Seoul (KR)

(72) Inventor: Cheong Woon Cho, Daejeon (KR)

(73) Assignee: CUSTOMEDI CO., LTD., Seoul (KR)

( * ) Notice: Subject to any disclaimer, the term of this patent is extended or adjusted under 35 U.S.C. 154(b) by 108 days.

(21) Appl. No.: 16/763,184

(22) PCT Filed: Nov. 22, 2019

(86) PCT No.: PCT/KR2019/016098
§ 371 (c)(1),
(2) Date: May 11, 2020

(87) PCT Pub. No.: WO2021/100929
PCT Pub. Date: May 27, 2021

(65) Prior Publication Data
US 2021/0401443 A1 Dec. 30, 2021

(30) Foreign Application Priority Data
Nov. 22, 2019 (KR) .......................... 10-2019-0150940

(51) Int. Cl.
*A61B 17/15* (2006.01)
*A61B 17/17* (2006.01)
(Continued)

(52) U.S. Cl.
CPC ............ *A61B 17/152* (2013.01); *A61B 17/17* (2013.01); *A61B 17/151* (2013.01);
(Continued)

(58) Field of Classification Search
CPC ....... A61B 17/152; A61B 17/15; A61B 17/17; A61B 17/68; A61B 17/80; A61B 17/8095;
(Continued)

(56) References Cited

U.S. PATENT DOCUMENTS 4,360,012 A * 11/1982 McHarrie .......... A61B 17/6441
606/54
5,921,988 A * 7/1999 Legrand ............. A61B 17/8095
606/87
(Continued)

FOREIGN PATENT DOCUMENTS

JP 2007075268 A 3/2007
KR 101451515 B1 10/2014

OTHER PUBLICATIONS

International search report of PCT/KR2019/016098, dated Aug. 21, 2020.

*Primary Examiner* — Marcela I. Shirsat
(74) *Attorney, Agent, or Firm* — STIP Law Group, LLC (57) ABSTRACT

The present invention relates to a guide module having oblique installation pins, the guide module including: a first installation pin unit penetratively inserted into one side of an aligned bone; a second installation pin unit penetratively inserted into the other side of the aligned bone; a reposition guide unit simultaneously penetrated by the first installation pin unit and the second installation pin unit and being simultaneously in contact with one side of the aligned bone and the other side of the aligned bone; and a compression guide unit disposed adjacent to the reposition guide unit and simultaneously penetrated by the first installation pin unit and the second installation pin unit, in which imaginary central axes of holes of the reposition guide unit penetrated by the first installation pin unit and the second installation pin unit are spaced apart, at a predetermined interval in a vertical direction, from imaginary central axes of holes of the compression guide unit. Therefore, the aligned bone may be compressed.

5 Claims, 11 Drawing Sheets

(51) Int. Cl.
    *A61B 17/84*    (2006.01)
    *A61B 17/66*    (2006.01)
    *A61B 17/80*    (2006.01)
    *A61B 17/68*    (2006.01)

(52) U.S. Cl.
    CPC ....... *A61B 17/1728* (2013.01); *A61B 17/1739* (2013.01); *A61B 17/66* (2013.01); *A61B 17/8004* (2013.01); *A61B 17/8095* (2013.01); *A61B 17/846* (2013.01); *A61B 2017/681* (2013.01)

(58) Field of Classification Search
    CPC ... A61B 17/86; A61B 17/846; A61B 17/1728; A61B 17/1739; A61B 17/151; A61B 17/66; A61B 17/7216; A61B 17/7225; A61B 17/8004; A61B 17/8014; A61B 2017/681
    USPC .................................. 606/87, 915, 86 B, 99
    See application file for complete search history.

(56) References Cited

U.S. PATENT DOCUMENTS

| | | | |
|---|---|---|---|
| 2006/0064087 A1* | 3/2006 | Mirza | A61B 17/6416 606/59 |
| 2009/0157086 A1 | 6/2009 | Digeser et al. | |
| 2010/0262193 A1 | 10/2010 | Frigg et al. | |
| 2017/0333102 A1* | 11/2017 | Peterson | A61B 17/1717 |
| 2018/0235798 A1 | 8/2018 | Taylor et al. | |

* cited by examiner

GUIDE MODULE HAVING OBLIQUE INSTALLATION PINS

CROSS-REFERENCE TO RELATED APPLICATIONS

This application is the U.S. National Phase under 35 U.S.C. § 371 of International Application No. PCT/KR2019/016098 filed on Nov. 22, 2019, which in turn claims the benefit of Korean Application No. 10-2019-0150940, filed on Nov. 22, 2019, the disclosures of which are incorporated by reference into the present application.

TECHNICAL FIELD

The present invention relates to a guide module having oblique installation pins, and more particularly, to a guide module having oblique installation pins, in which central axes of holes of a reposition guide and central axes of holes of a compression guide or a fixing guide are not coincident with each other, such that the installation pins, which penetrate all of the holes, are oblique and thus may compress an aligned bone and coupling force between a reposition guide unit and the installation pins may be increased.

BACKGROUND ART

The knee has one of the largest joints in the body and plays an important role in daily life. The knee is divided into three sections including a proximal section, a distal section, and a patellar/femoral section.

Degenerative osteoarthritis affects only one section of the knee, and in most cases, the proximal section is usually most commonly damaged. In case of such asymmetrical damage, the osteotomy serves to move the weight bearing line to a healthy section to relieve pain and slow the progression of arthritis.

Corrective osteotomy for treating degenerative osteoarthritis is broadly classified into closing osteotomy and opening osteotomy. The closing osteotomy is a method that removes a wedge-shaped bone segment and then closes a gap. The opening osteotomy is a method that opens a bone to the extent that deformation is needed, fixes the bone with a metal material, and then performs bone grafting in an opened gap.

FIGS. 1 to 4 are views illustrating a surgical procedure of the corrective osteotomy in the related art. Hereinafter, a surgical procedure and a problem of the corrective osteotomy in the related art will be described with reference to FIGS. 1 to 4.

Figure 1:
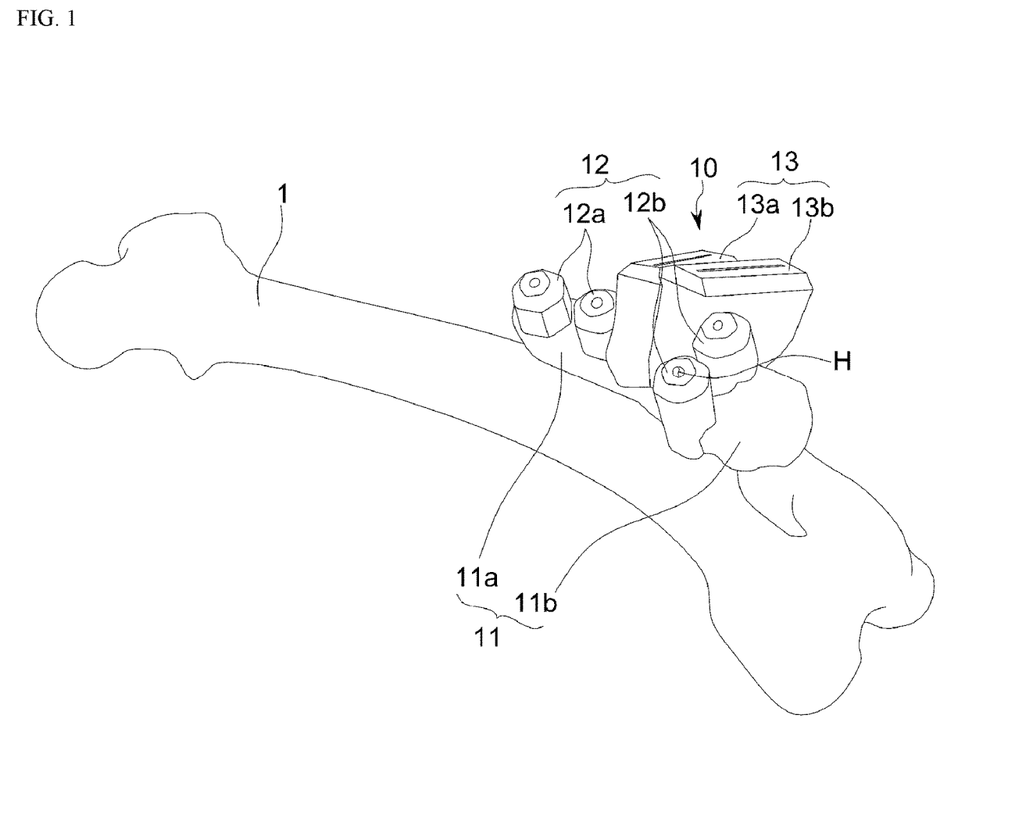
FIG. 1, FIG. 2, FIG. 3 and FIG. 4 are views illustrating a surgical procedure of the corrective osteotomy in the related art.

First, as illustrated in FIG. 1, a surgical guide 10 for osteotomy is matched with a bone 1. The surgical guide 10 includes support portions 11, drilling guides 12, and cutting guides 13. The support portions 11 are complementarily coupled to a surface of the bone 1. The pair of support portions 11, the pair of drilling guides 12, and the pair of cutting guides 13 are provided at one side and the other side based on a site to be subjected to osteotomy.

Figure 2:
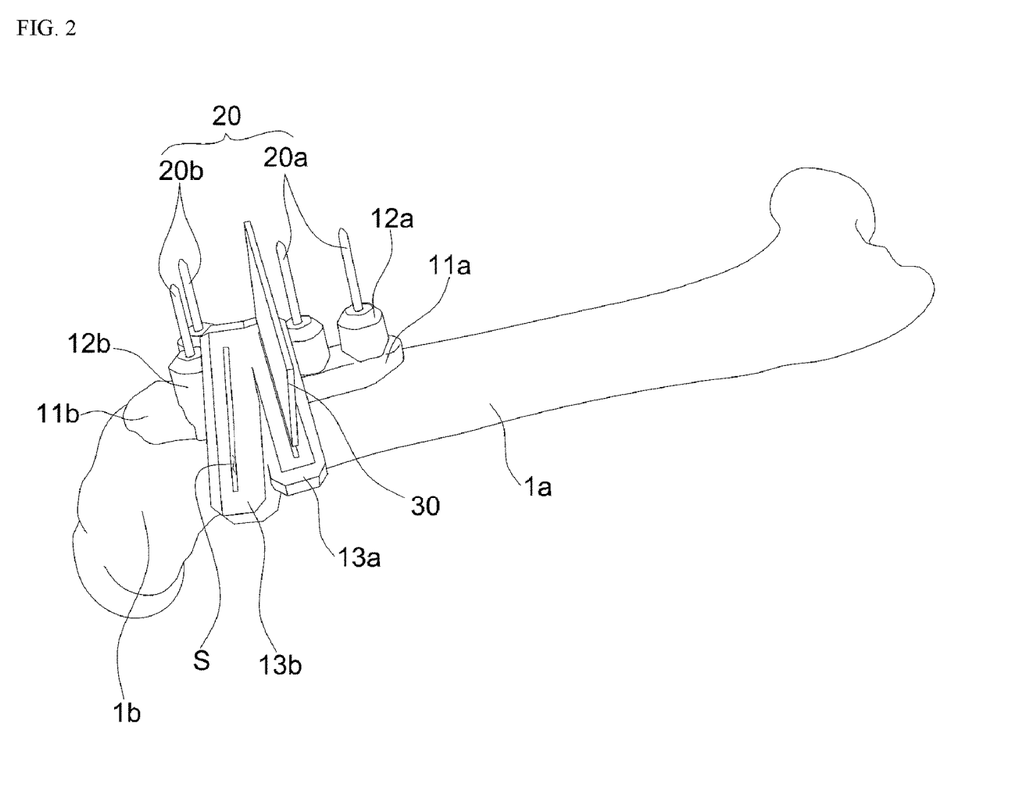

The operator penetratively inserts installation pins 20 into holes H formed in the drilling guides 12 to temporarily fix the surgical guide 10 and the bone 1, and cuts the bone 1 by inserting cutters 30 into slots S formed in the cutting guides 13, as illustrated in FIG. 2. In this case, the pair of cutting guides 13 has an angle therebetween so that the bone 1 to be subjected to the osteotomy has a wedge shape.

Figure 3:
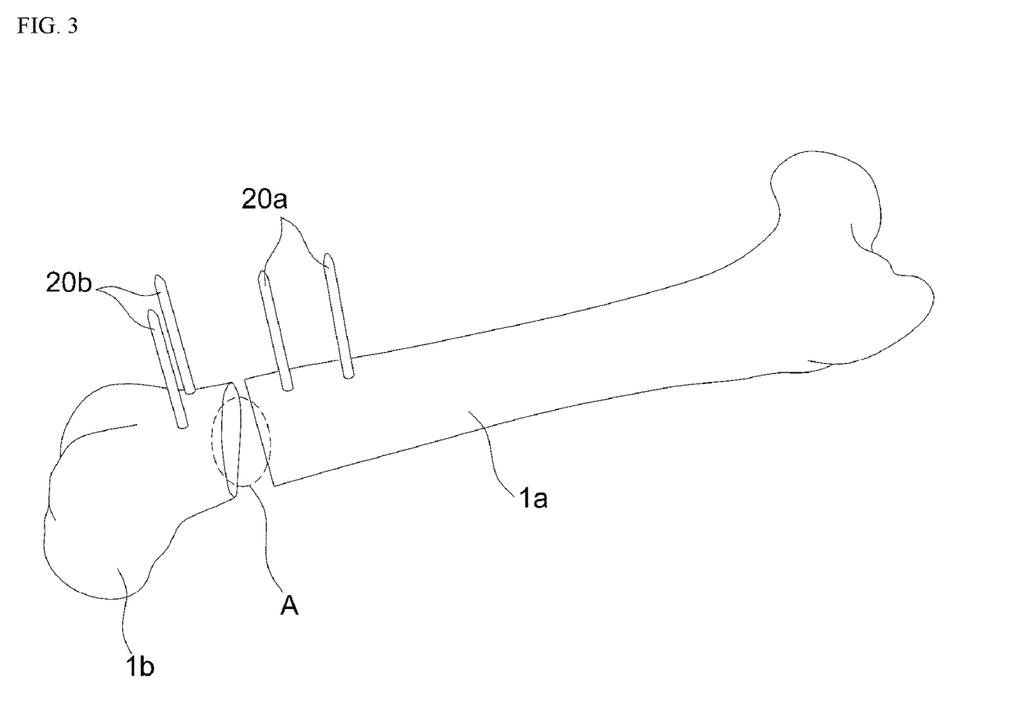
Figure 4:
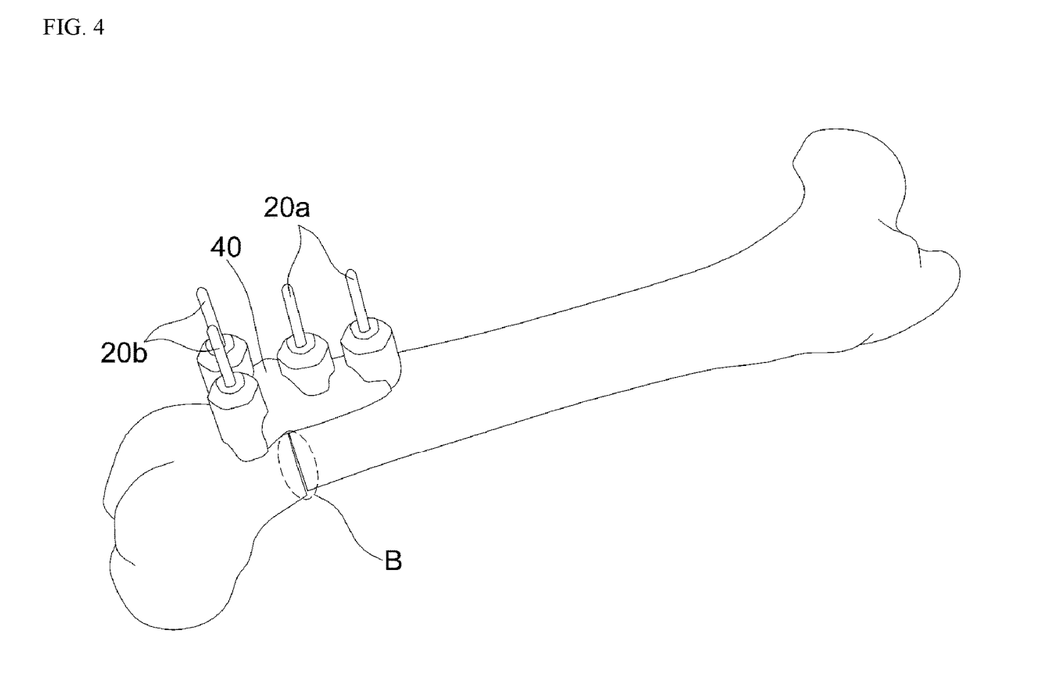

Next, when the operator removes the surgical guide 10, the bone 1 is separated into two bones 1a and 1b at a cut site A, as illustrated in FIG. 3. As illustrated in FIG. 4, the two bones 1a and 1b are aligned (an alignment site (or osteotomy site) 'B' is formed), and a reposition guide 40 is coupled along the installation pins 20. The reposition guide 40 serves to maintain the aligned two bones 1a and 1b in accordance with a surgical plan.

However, all the plurality of installation pins 20 coupled to the reposition guide 40 in the related art is generally parallel to one another, and the reposition guide 40 is often slipped off along the parallel installation pins 20. For this reason, the reposition guide 40 cannot properly serve to maintain the aligned two bones 1a and 1b in accordance with the surgical plan, such that after the surgical procedure is completed, the bone 1 is not properly aligned or the gap between the two bones 1a and 1b is not be sufficiently decreased at the osteotomy site B, which causes a problem in that the bone 1 is slowly joined during a process of healing the bone 1 after the surgical procedure. Accordingly, there is a need for a method capable of properly maintaining the alignment between the bone 1 and surgical tools associated with the use of the reposition guide 40, and there is also a need for an invention capable of sufficiently decreasing the gap in the bone 1 after the surgical procedure.

DOCUMENT OF RELATED ART

Patent Document (Patent Document 1) Korean Patent No. 10-1451515

DISCLOSURE

Technical Problem

The present invention relates to a guide module having oblique installation pins, and more particularly, to a guide module having oblique installation pins, in which central axes of holes of a reposition guide and central axes of holes of a compression guide or a fixing guide are not coincident with each other, such that the installation pins, which penetrate all of the holes, are oblique and thus may compress an aligned bone and coupling force between a reposition guide unit and the installation pins may be increased.

Technical Solution

In order to achieve the above-mentioned object, a guide module having oblique installation pins according to the present invention includes: a first installation pin unit penetratively inserted into one side of an aligned bone; a second installation pin unit penetratively inserted into the other side of the aligned bone; a reposition guide unit simultaneously penetrated by the first installation pin unit and the second installation pin unit and being simultaneously in contact with one side of the aligned bone and the other side of the aligned bone; and a compression guide unit disposed adjacent to the reposition guide unit and simultaneously penetrated by the first installation pin unit and the second installation pin unit, in which imaginary central axes of holes of the reposition guide unit penetrated by the first installation pin unit and the second installation pin unit are spaced apart, at a predetermined interval in a vertical direction, from imaginary central axes of holes of the compression guide unit.

In the guide module having oblique installation pins according to the present invention, the imaginary central axis of the hole of the reposition guide unit penetrated by the first installation pin unit may be positioned more proximally than the imaginary central axis of the hole of the compression guide unit penetrated by the first installation pin unit.

In the guide module having oblique installation pins according to the present invention, the imaginary central axis of the hole of the reposition guide unit penetrated by the second installation pin unit may be positioned more proximally than the imaginary central axis of the hole of the compression guide unit penetrated by the second installation pin unit.

In the guide module having oblique installation pins according to the present invention, the pair of first installation pin units and the pair of second installation pin units may be provided. In addition, a guide module having oblique installation pins according to another exemplary embodiment of the present invention includes: a pair of first installation pin units penetratively inserted into one side of an aligned bone; a pair of second installation pin units penetratively inserted into the other side of the aligned bone; a reposition guide unit simultaneously penetrated by the first installation pin units and the second installation pin units and being simultaneously in contact with one side of the aligned bone and the other side of the aligned bone; and a fixing guide unit disposed adjacent to the reposition guide unit and simultaneously penetrated by the pair of first installation pin units, in which imaginary central axes of a pair of holes of the reposition guide unit penetrated by the pair of first installation pin units are spaced apart, at a predetermined interval in a vertical direction, from imaginary central axes of a pair of holes of the fixing guide unit.

Advantageous Effects

According to the exemplary embodiment of the present invention, the first installation pin units and the second installation pin units penetrate the compression guide unit, the first installation pin units, which are positioned at the upper side based on the alignment site, are in the form of an oblique line inclined in the direction from the upper side to the lower side, and the second installation pin units, which are positioned at the lower side based on the alignment site, are in the form of an oblique line inclined in the direction from the lower side to the upper side, such that the alignment site of the bone may be compressed.

In addition, according to the exemplary embodiment of the present invention, the first installation pin units penetrate the fixing guide unit, the first-of-first installation pin unit, which is positioned at the upper side based on the reposition guide unit, is in the form of an oblique line inclined in the direction from the upper side to the lower side, and the second-of-first installation pin unit, which is positioned at the lower side based on the reposition guide unit, is in the form of an oblique line inclined in the direction from the lower side to the upper side, such that coupling force between the reposition guide unit and the first installation pin units is increased.

BEST MODE

Hereinafter, exemplary embodiments of the present invention will be described in detail so that those with ordinary skill in the art to which the present invention pertains may easily carry out the exemplary embodiments. However, the present invention may be implemented in various different ways and is not limited to the exemplary embodiments described herein.

A guide module according to the present invention includes first installation pin units $20a$, second installation pin units $20b$, a reposition guide unit 40, and a compression guide unit 100. Hereinafter, a configuration and an effect of the guide module according to the present invention will be described with reference to FIG. 5.

Figure 5:
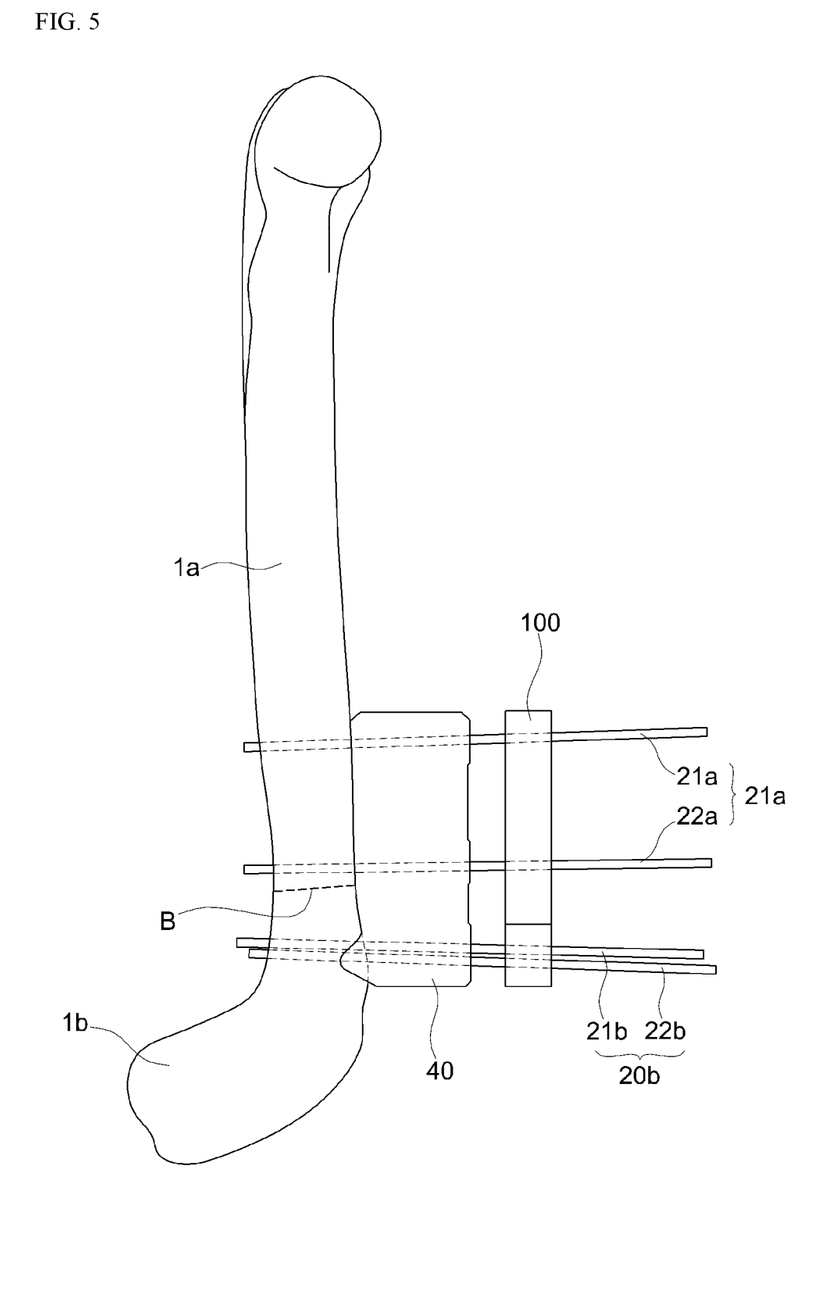
FIG. 5 is a view illustrating a guide module according to the present invention.

The pair of first installation pin units $20a$ may be provided and penetratively inserted into one side $1a$ of a bone. However, the present invention is not limited to the number of first installation pin units $20a$. In addition, the first installation pin units $20a$ include a first-of-first installation pin unit $21a$ and a second-of-first installation pin unit $22a$. The first-of-first installation pin unit $21a$ is positioned more distally than the second-of-first installation pin unit $22a$ based on an alignment site B where one side $1a$ of the bone and the other side $1b$ of the bone are aligned. Hereinafter, the terms 'proximal' and 'distal' are defined based on the alignment site B where one side $1a$ of the bone and the other side $1b$ of the bone are aligned.

As described below, the pair of first installation pin units $20a$ is disposed in the form of an oblique line so that ends of the pair of first installation pin units $20a$ become closer to the alignment site B.

The pair of second installation pin units $20b$ may be provided and penetratively inserted into the other side $1b$ of the bone. However, the present invention is not limited to the number of second installation pin units $20b$. In addition, like the first installation pin units $20a$, the second installation pin units $20b$ include a first-of-second installation pin unit $21b$ and a second-of-second installation pin unit $22b$.

As described below, the pair of second installation pin units $20b$ is disposed in the form of an oblique line so that ends of the pair of second installation pin units $20b$ become closer to the alignment site B.

The reposition guide unit 40 is penetrated simultaneously by the first installation pin units $20a$ and the second installation pin units $20b$. In addition, the reposition guide unit 40 is in contact with both of one side 1a of the bone and the other side 1b of the bone. Therefore, the reposition guide unit 40 serves to support the alignment between one side 1a of the bone and the other side 1b of the bone.

The reposition guide unit 40 has first reposition guide unit holes 41 penetrated by the first installation pin units 20a, and second reposition guide unit holes 42 penetrated by the second installation pin units 20b.

In the case in which the pair of first installation pin units 20a is provided, the pair of first reposition guide unit holes 41 is also provided and includes a first-of-first reposition guide unit hole 41a and a second-of-first reposition guide unit hole 41b. In addition, the second-of-first reposition guide unit hole 41b is formed more proximally than the first-of-first reposition guide unit hole 41a.

Likewise, in the case in which the pair of second installation pin units 20b is provided, the pair of second reposition guide unit holes 42 is also provided and includes a first-of-second reposition guide unit hole 42a and a second-of-second reposition guide unit hole 42b. In this case, the first-of-second reposition guide unit hole 42a and the second-of-second reposition guide unit hole 42b may be positioned on the same line in a width direction.

All of the first-of-first reposition guide unit hole 41a, the second-of-first reposition guide unit hole 41b, the first-of-second reposition guide unit hole 42a, and the second-of-second reposition guide unit hole 42b have imaginary central axes, respectively. This configuration will be described in detail below.

Figure 6:
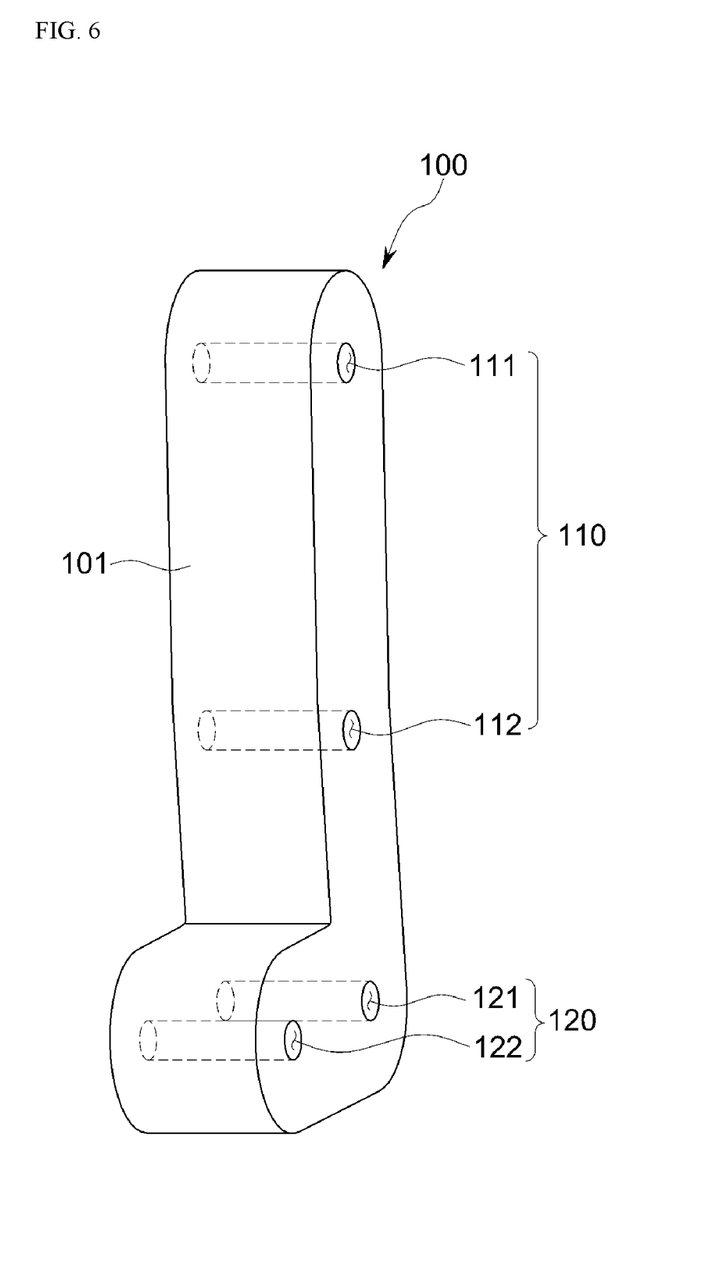
FIG. 6 is a view illustrating a compression guide unit according to the present invention.

FIG. 6 is a view illustrating the compression guide unit 100 according to the present invention.

Both the first installation pin unit 20a and the second installation pin unit 20b are penetratively inserted into the compression guide unit 100, and the compression guide unit 100 is positioned adjacent to the reposition guide unit 40.

The compression guide unit 100 includes a compression guide unit main body 101, and a plurality of holes penetrated by the first installation pin units 20a and the second installation pin units 20b. The plurality of holes includes first compression guide unit holes 110 and second compression guide unit holes 120. The first compression guide unit holes 110 are formed at positions corresponding to the first reposition guide unit holes 41, and the second compression guide unit holes 120 are formed at positions corresponding to the second reposition guide unit holes 42.

Therefore, the pair of first compression guide unit holes 110 and the pair of second compression guide unit holes 120 are provided. The first compression guide unit holes 110 include a first-of-first compression guide unit hole 111 and a second-of-first compression guide unit hole 112. In this case, like the first reposition guide unit holes 41, the second-of-first compression guide unit hole 112 is positioned more proximally than the first-of-first compression guide unit hole 111.

Likewise, the second compression guide unit holes 120 include a first-of-second compression guide unit hole 121 and a second-of-second compression guide unit hole 122. In this case, the first-of-second compression guide unit hole 121 and the second-of-second compression guide unit hole 122 are positioned on the same line in the width direction.

All of the first-of-first compression guide unit hole 111, the second-of-first compression guide unit hole 112, the first-of-second compression guide unit hole 121, and the second-of-second compression guide unit hole 122 have imaginary central axes, respectively. This configuration will be described in detail below.

Figure 7:
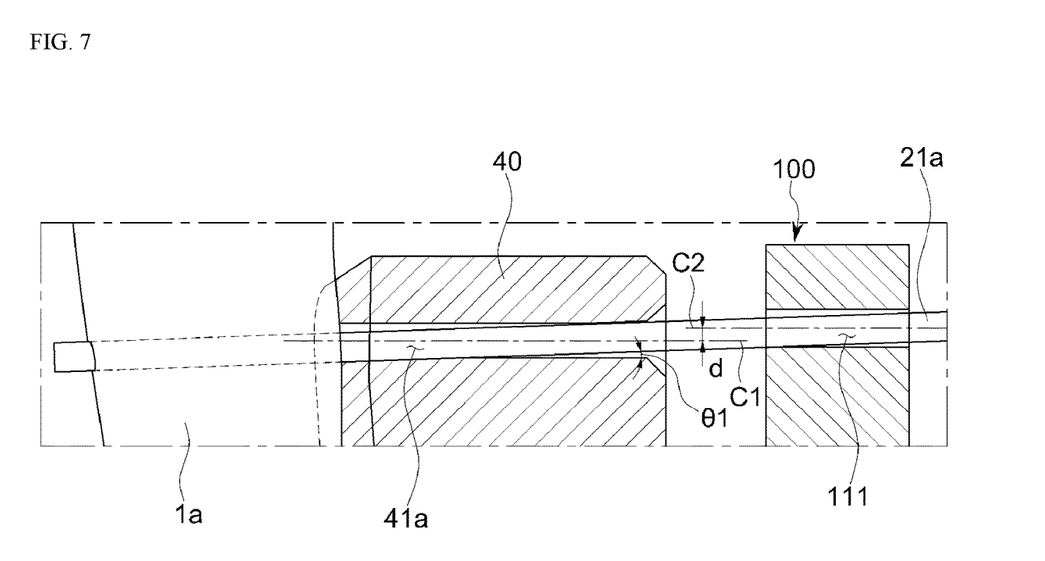
FIG. 7 is a view illustrating a state in which a first-of-first installation pin unit according to the present invention is penetratively inserted sequentially and simultaneously into a first-of-first compression guide unit hole, a first-of-first reposition guide unit hole, and one side of a bone.

FIG. 7 is a view illustrating a state in which the first-of-first installation pin unit 21a is penetratively inserted sequentially and simultaneously into the first-of-first compression guide unit hole 111, the first-of-first reposition guide unit hole 41a, and one side 1a of the bone.

As illustrated in FIG. 7, the imaginary central axis C1 of the first-of-first reposition guide unit hole 41a penetrated by the first-of-first installation pin unit 21a is spaced apart, at a predetermined interval d in a vertical direction, from the imaginary central axis C2 of the first-of-first compression guide unit hole 111 penetrated by the first-of-first installation pin unit 21a. In addition, the imaginary central axis C1 of the first-of-first reposition guide unit hole 41a is positioned more proximally than the imaginary central axis C2 of the first-of-first compression guide unit hole 111.

Figure 8:
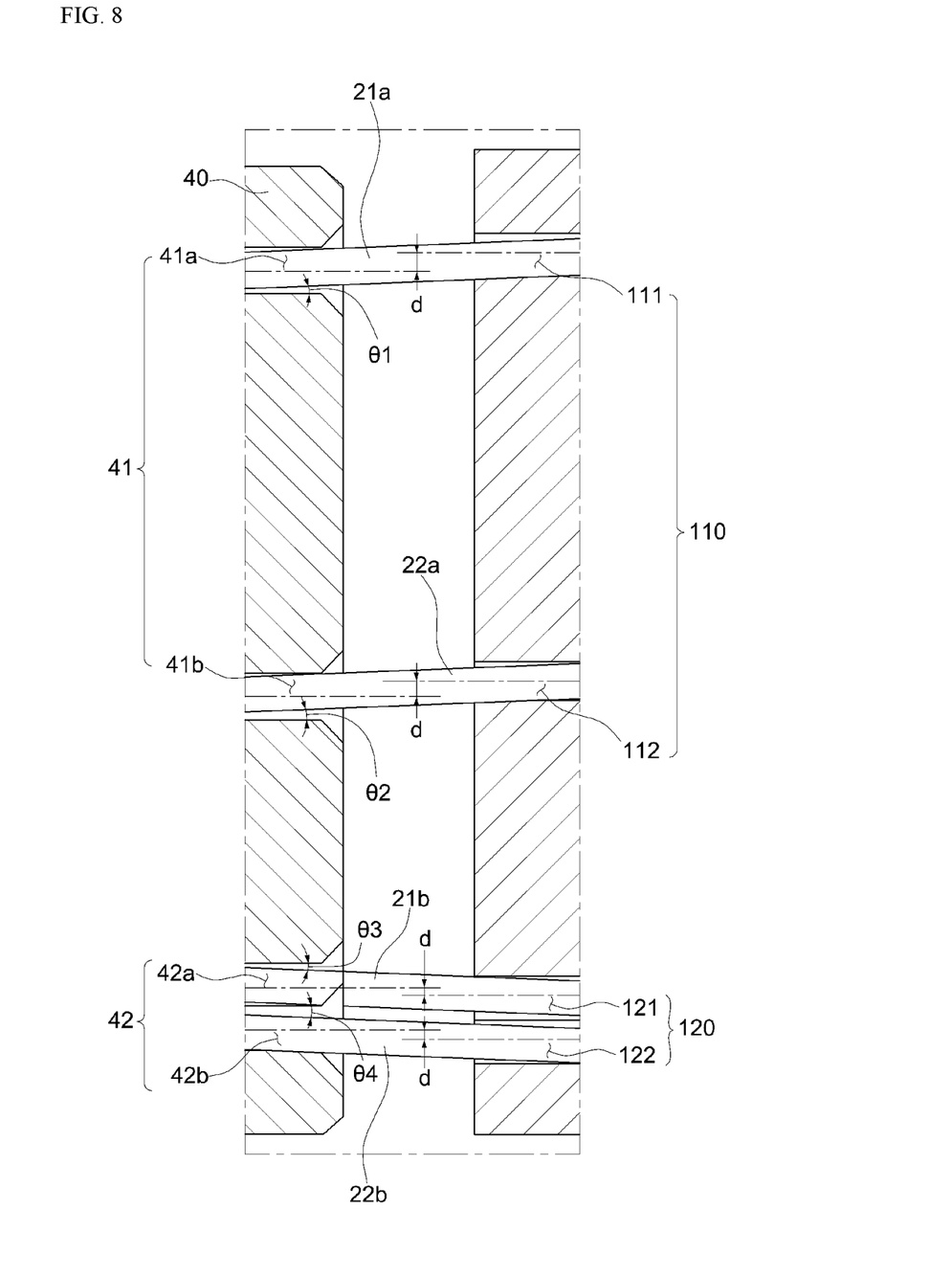
FIG. 8 is an enlarged view of a first installation pin unit and a second installation pin unit according to the present invention.

With this configuration, the first-of-first installation pin unit 21a sequentially penetrates the first-of-first compression guide unit hole 111, the first-of-first reposition guide unit hole 41a, and one side 1a of the bone so that the end of the first-of-first installation pin unit 21a is penetratively inserted in the form of an oblique line directed toward the alignment site B, as illustrated in FIG. 8. As an example, the first-of-first installation pin unit 21a is inclined in a direction from an upper side to a lower side while having a predetermined angle θ1 with respect to the imaginary central axis C1 of the first-of-first reposition guide unit hole 41a.

FIG. 8 is an enlarged view of the first installation pin units 20a and the second installation pin units 20b.

Like the first-of-first installation pin unit 21a formed in the form of an oblique line, the imaginary central axis of the second-of-first reposition guide unit hole 41b penetrated by the second-of-first installation pin unit 22a is spaced apart, at the predetermined interval d in the vertical direction, from the imaginary central axis of the second-of-first compression guide unit hole 112 penetrated by the second-of-first installation pin unit 22a. In addition, the imaginary central axis of the second-of-first reposition guide unit hole 41b is positioned more proximally than the imaginary central axis of the second-of-first compression guide unit hole 112.

Therefore, like the first-of-first installation pin unit 21a, the end of the second-of-first installation pin unit 22a is penetratively inserted in the form of an oblique line directed toward the alignment site B. As an example, the second-of-first installation pin unit 22a is inclined while having a predetermined angle θ2 with respect to the imaginary central axis of the second-of-first reposition guide unit hole 41b.

In addition, the imaginary central axis of the first-of-second reposition guide unit hole 42a penetrated by the first-of-second installation pin unit 21b is spaced apart, at the predetermined interval d in the vertical direction, from the imaginary central axis of the first-of-second compression guide unit hole 121 penetrated by the first-of-second installation pin unit 21b. In addition, the imaginary central axis of the first-of-second reposition guide unit hole 42a is positioned more proximally than the imaginary central axis of the first-of-second compression guide unit hole 121.

In this case, unlike the first reposition guide unit holes 41 and the first compression guide unit holes 110, the second reposition guide unit holes 42 and the second compression guide unit holes 120 are positioned at the lower side from the alignment site B. Therefore, in the case in which the imaginary central axis of the first-of-second reposition guide unit hole 42a is positioned more proximally than the imaginary central axis of the first-of-second compression guide unit hole 121, the first-of-second installation pin unit 21b, which sequentially penetrates the first-of-second compression guide unit hole 121, the first-of-second reposition guide unit hole 42a, and the other side 1b of the bone, is inclined in the direction from the lower side to the upper side, unlike the first installation pin unit 20a. Based on FIG. 8, the first-of-second installation pin unit 21b is inclined in the direction from the lower side to the upper side while having a predetermined angle θ3 with respect to the imaginary central axis of the first-of-second reposition guide unit hole 42a.

As described above, since the second-of-second installation pin unit 22b and the first-of-second installation pin unit 21b are positioned on the same line in the width direction, the second-of-second installation pin unit 22b is also inclined in the direction from the lower side to the upper side, like the first-of-second installation pin unit 21b. Based on FIG. 8, the second-of-second installation pin unit 22b is inclined in the direction from the lower side to the upper side while having a predetermined angle θ4 with respect to the imaginary central axis of the second-of-second reposition guide unit hole 42b.

With this arrangement, as illustrated in FIG. 4, based on the alignment site B, the first installation pin unit 20a is in the form of an oblique line inclined in the direction from the upper side to the lower side, and the second installation pin unit 20b is in the form of an oblique line inclined in the direction from the lower side to the upper side. Therefore, the first installation pin units 20a and the second installation pin units 20b press, in the opposite directions, the alignment site B of the bone, thereby compressing the alignment site B of the bone. In addition, the reposition guide unit 40 and the compression guide unit 50, which are penetrated by the first installation pin units 20a and the second installation pin units 20b, are also compressed and thus hardly withdrawn. Therefore, unlike the parallel installation pins in the related art, the alignment site B of the bone is compressed, and the reposition guide unit 40 and the compression guide unit 50 are hardly withdrawn, such that fixing force is increased.

Figure 9:
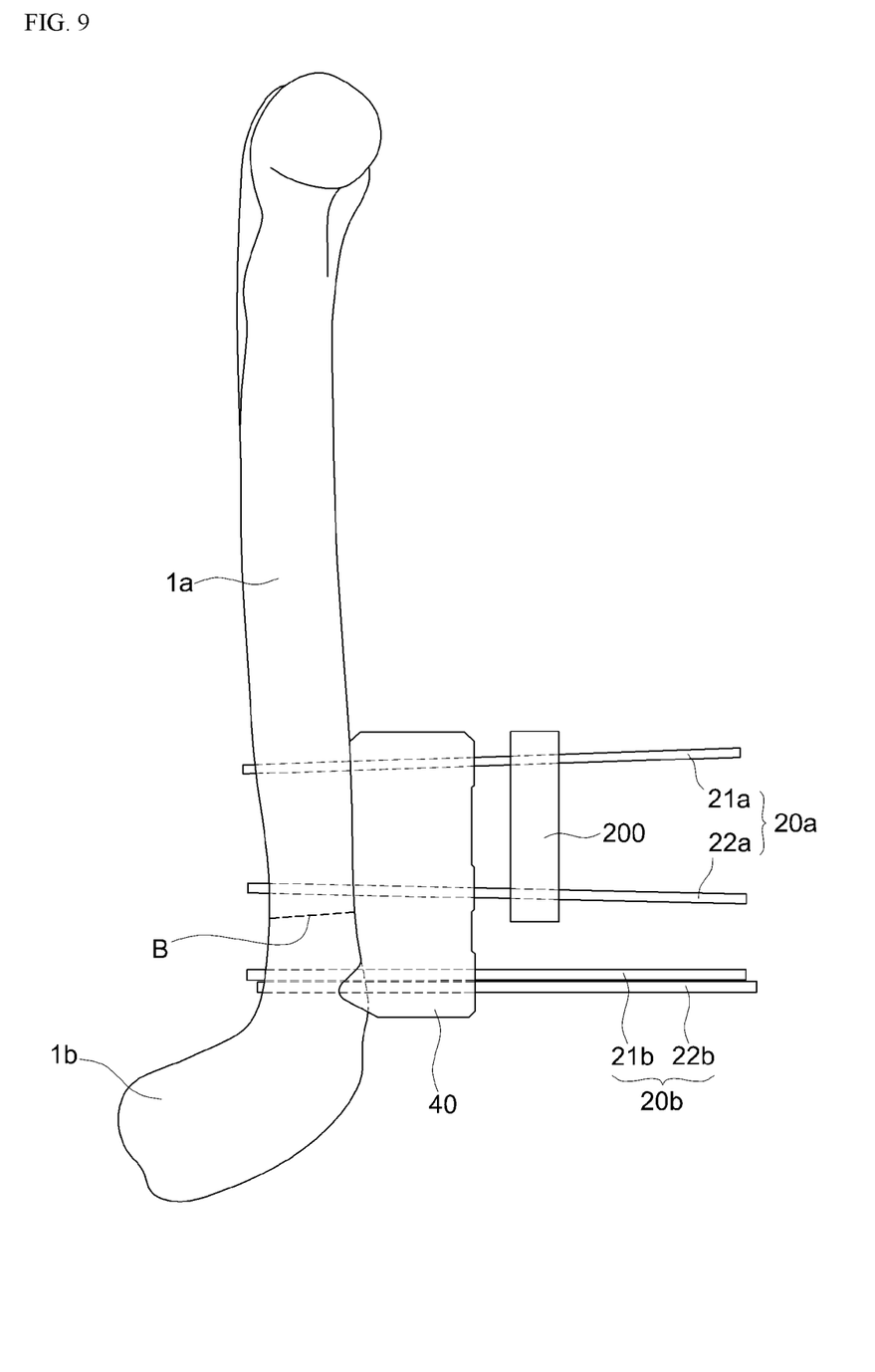
FIG. 9 is a view illustrating a configuration of a guide module according to another exemplary embodiment of the present invention.

FIG. 9 is a view illustrating a configuration of a guide module according to another exemplary embodiment of the present invention.

In the case of the guide module according to another exemplary embodiment, only the first installation pin units 20a are inserted into the compression guide unit 100. For convenience of description, hereinafter, the compression guide unit according to another exemplary embodiment is referred to as a fixing guide unit 200.

Figure 10:
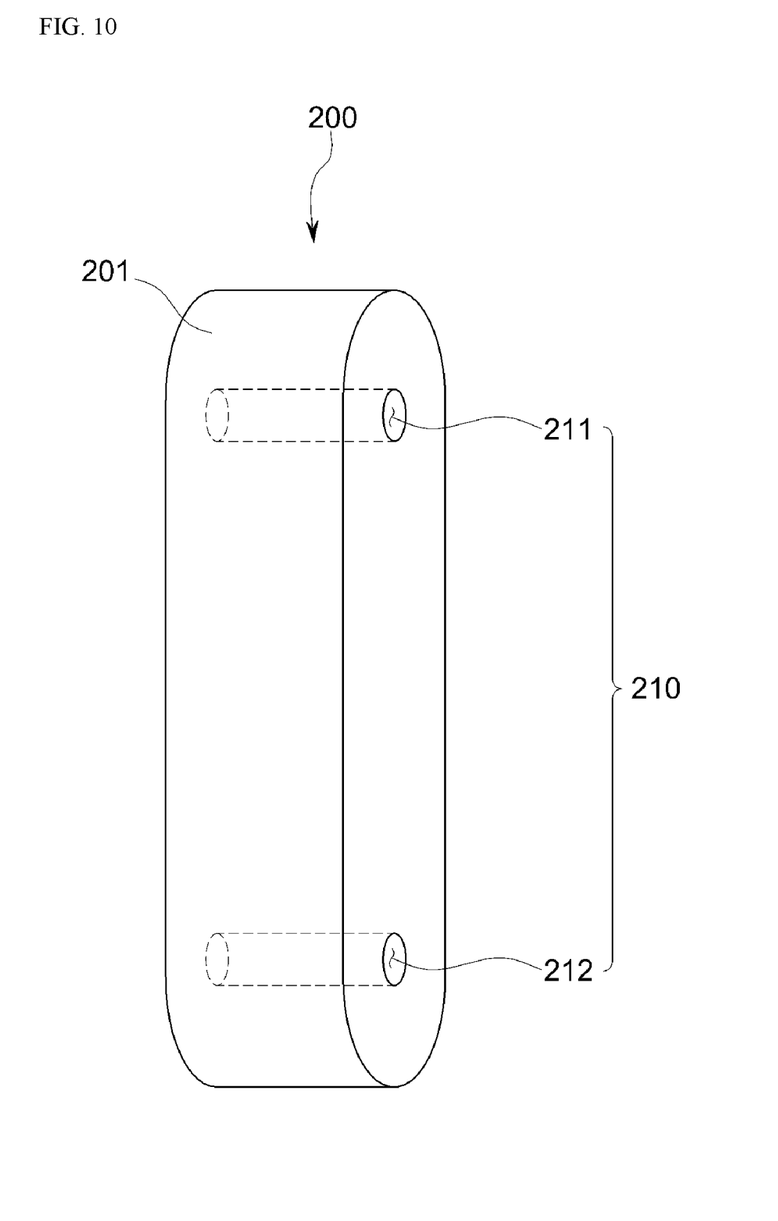
FIG. 10 is a view illustrating a fixing guide unit according to the present invention.

FIG. 10 is a view illustrating the fixing guide unit 200 according to the present invention.

The fixing guide unit 200 is disposed adjacent to the reposition guide unit 40 and penetrated by the pair of first installation pin units 20a.

The fixing guide unit 200 has a fixing guide unit main body 201 and fixing guide unit holes 210. The pair of fixing guide unit holes 210 is provided and includes a first fixing guide unit hole 211 and a second fixing guide unit hole 212. The first fixing guide unit hole 211 is penetrated by the first-of-first installation pin unit 21a, and the second fixing guide unit hole 212 is penetrated by the second-of-first installation pin unit 22a.

Figure 11:
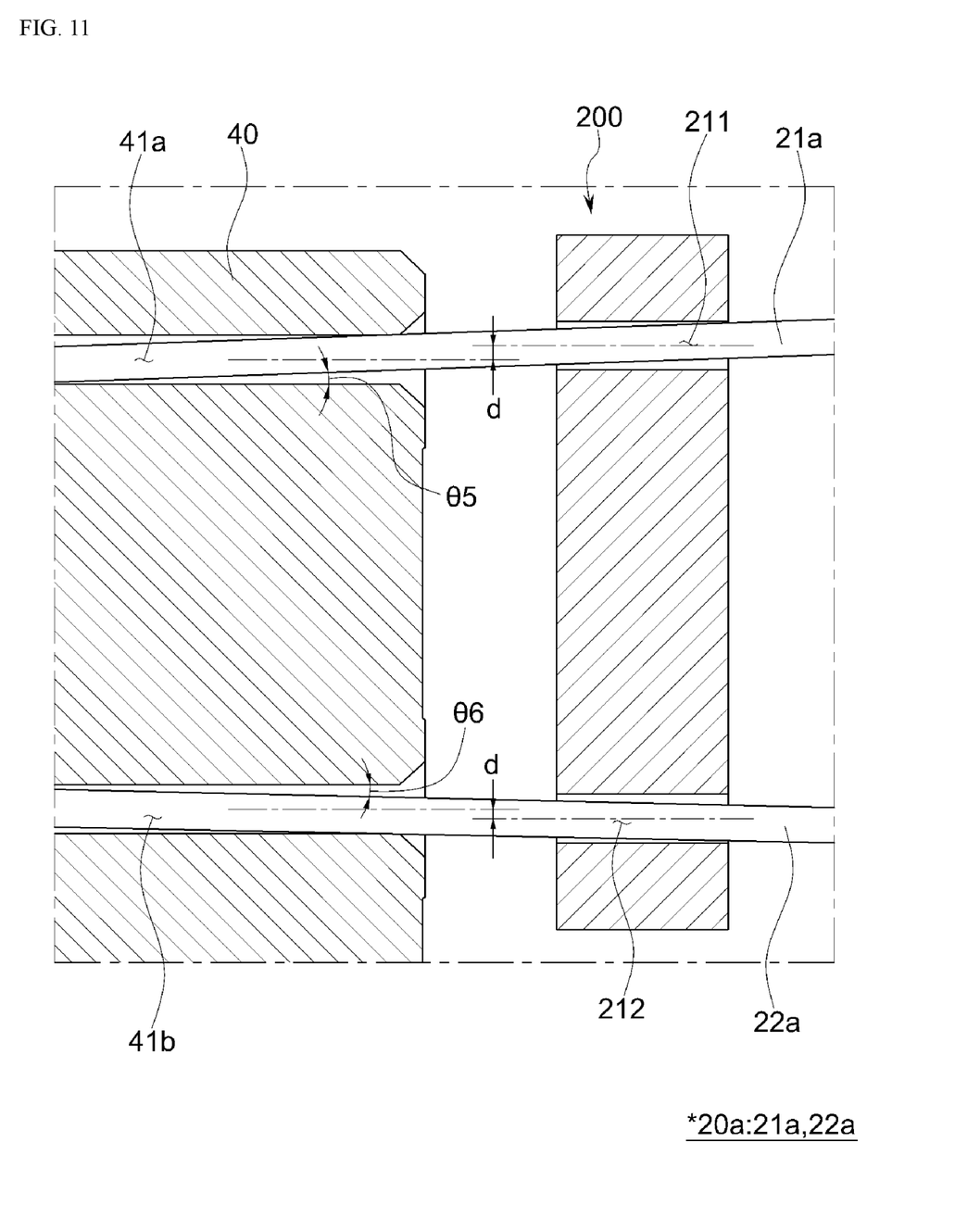
FIG. 11 is an enlarged view illustrating a state in which the first-of-first installation pin unit sequentially penetrates a first fixing guide unit hole, the first-of-first reposition guide unit hole, and one side of the bone and a second-of-first installation pin unit sequentially penetrates a second fixing guide unit hole, a second-of-first reposition guide unit hole, and one side of the bone.

FIG. 11 is an enlarged view illustrating a state in which the first-of-first installation pin unit 21a sequentially penetrates the first fixing guide unit hole 211, the first-of-first reposition guide unit hole 41a, and one side 1a of the bone, and the second-of-first installation pin unit 22a sequentially penetrates the second fixing guide unit hole 212, the second-of-first reposition guide unit hole 41b, and one side 1a of the bone.

Unlike the compression guide unit 100, the fixing guide unit 200 is penetrated only by the first installation pin units 20a. As illustrated in FIG. 11, the imaginary central axis of the first-of-first reposition guide unit hole 41a penetrated by the first-of-first installation pin unit 21a is spaced apart, at the predetermined interval d in the vertical direction, from the imaginary central axis of the first fixing guide unit hole 211 penetrated by the first-of-first installation pin unit 21a. In addition, the imaginary central axis of the first-of-first reposition guide unit hole 41a is positioned more proximally than the imaginary central axis of the first fixing guide unit hole 211. With this configuration, the first-of-first installation pin unit 21a sequentially penetrates the first fixing guide unit hole 211, the first-of-first reposition guide unit hole 41a, and one side 1a of the bone so that the end of the first-of-first installation pin unit 21a is penetratively inserted in the form of an oblique line directed toward the alignment site B. As an example, the first-of-first installation pin unit 21a is inclined in the direction from the upper side to the lower side while having a predetermined angle θ5 with respect to the imaginary central axis of the first-of-first reposition guide unit hole 41a.

In this case, unlike the compression guide unit 100, the second-of-first installation pin unit 22a is inclined in the direction from the lower side to the upper side. The imaginary central axis of the second-of-first reposition guide unit hole 41b penetrated by the second-of-first installation pin unit 22a is spaced apart, at the predetermined interval d in the vertical direction, from the imaginary central axis of the second fixing guide unit hole 212 penetrated by the second-of-first installation pin unit 22a. In addition, the central axis of the second-of-first reposition guide unit hole 41b is positioned more distally than the imaginary central axis of the second fixing guide unit hole 212. With this configuration, the second-of-first installation pin unit 22a sequentially penetrates the second fixing guide unit hole 212, the second-of-first reposition guide unit hole 41a, and one side 2a of the bone so that the end of the second-of-first installation pin unit 22a is penetratively inserted in the form of an oblique line directed toward the alignment site B. As an example, the second-of-first installation pin unit 22a is inclined in the direction from the lower side to the upper side while having a predetermined angle θ6 with respect to the imaginary central axis of the second-of-first reposition guide unit hole 41b.

With this arrangement, as illustrated in FIG. 9, the first-of-first installation pin unit 21a is in the form of an oblique line inclined in the direction from the upper side to the lower side, and the second-of-first installation pin unit 22a is in the form of an oblique line inclined in the direction from the lower side to the upper side. Therefore, unlike the exemplary embodiment, the first installation pin units 20a compress the reposition guide unit 40 instead of the alignment site B of the bone. Therefore, coupling force and fixing force between the reposition guide unit 40 and the first installation pin units 20a are increased. The operator may selectively utilize the compression guide unit 100 and the fixing guide unit 200 in accordance with environments.

Although preferred examples of the present invention have been described in detail hereinabove, the right scope of the present invention is not limited thereto, and it should be clearly understood that many variations and modifications of those skilled in the art using the basic concept of the present invention, which is defined in the following claims, will also belong to the right scope of the present invention.

INDUSTRIAL APPLICABILITY

The present invention relates to a guide module having oblique installation pins, and more particularly, to a guide module having oblique installation pins, in which central axes of holes of a reposition guide and central axes of holes of a compression guide or a fixing guide are not coincident with each other, such that the installation pins, which penetrate all of the holes, are oblique and thus may compress an aligned bone or increase coupling force between a reposition guide unit and the installation pins.

The invention claimed is:

1. A guide module having oblique installation pins, the guide module comprising:
   a first installation pin unit comprising a first pin and a second pin;
   a second installation pin unit comprising a third pin and a fourth pin;
   a reposition guide unit configured to be in direct contact with an aligned bone having an osteotomy site,
   wherein,
   the reposition guide unit is configured to be in direct contact with both one side and an opposite side of the aligned bone with respect to the osteotomy site, and
   the reposition guide unit has a first reposition hole with a first central reposition hole axis, a second reposition hole with a second central reposition hole axis, a third reposition hole with a third central reposition hole axis, and a fourth reposition hole with a fourth central reposition hole axis; and
   a compression guide unit disposed adjacent to the reposition guide unit,
   wherein the compression guide unit has a first compression hole with a first central compression hole axis, a second compression hole with a second central compression hole axis, a third compression hole with a third central compression hole axis, and a fourth compression hole with a fourth central compression hole axis,
   wherein,
   the first pin is configured to simultaneously pass through the first reposition hole, the first compression hole, and a portion of the aligned bone,
   the second pin is configured to simultaneously pass through the second reposition hole, the second compression hole, and another portion of the aligned bone,
   the third pin is configured to simultaneously pass through the third reposition hole, the third compression hole, and another portion of the aligned bone,
   the fourth pin is configured to simultaneously pass through the fourth reposition hole, the fourth compression hole, and another portion of the aligned bone,
   the first pin and the second pin are located on the one side with respect to the osteotomy site,
   the second pin is located closer to the osteotomy site than the first pin,
   the third pin and the fourth pin are located on the opposite side with respect to the osteotomy site, and
   the first central reposition hole axis is spaced apart at a predetermined distance from the first central compression hole axis such that the first pin is tilted with respect to the first central compression hole axis when the first pin passes through the first reposition hole and the first compression hole,
   the second central reposition hole axis is spaced apart at a predetermined distance from the second central compression hole axis such that the second pin is tilted with respect to the second central compression hole axis when the second pin passes through the second reposition hole and the second compression hole,
   the third central reposition hole axis is spaced apart at a predetermined distance from the third central compression hole axis such that the third pin is tilted with respect to the third central compression hole axis when the third pin passes through the third reposition hole and the third compression hole,
   the fourth central reposition hole axis is spaced apart at a predetermined distance from the fourth central compression hole axis such that the fourth pin is tilted with respect to the fourth central compression hole axis when the fourth pin passes through the fourth reposition hole and the fourth compression hole.

2. The guide module of claim 1, wherein the first central reposition hole axis is shifted toward the osteotomy site more than than the first central compression hole axis and the second central reposition hole axis is shifted toward the osteotomy site more than the second central compression hole axis.

3. The guide module of claim 2, wherein the third central reposition hole axis is shifted toward the osteotomy site more than the third central compression hole axis and the fourth central reposition hole axis is shifted toward the osteotomy site more than the fourth central compression hole axis.

4. A guide module having oblique installation pins, the guide module comprising:
   a first installation pin unit comprising a first pin and a second pin;
   a second installation pin unit comprising a third pin and a fourth pin;
   a reposition guide unit configured for direct contact with an aligned bone having an osteotomy site,
   wherein
   the reposition guide unit is configured to be in direct contact with both one side and an opposite side of the aligned bone with respect to the osteotomy site, and
   the reposition guide unit has a first reposition hole with a first central reposition hole axis, a second reposition hole with a second central reposition hole axis, a third reposition hole with a third central reposition hole axis, and a fourth reposition hole with a fourth central reposition hole axis; and
   a fixing guide unit disposed adjacent to the reposition guide unit, wherein the fixing guide unit has a first fixing hole with a first central fixing hole axis and a second fixing hole with a second central fixing hole axis,
   wherein,
   the first pin is configured to simultaneously pass through the first reposition hole, the first fixing hole, and a portion of the aligned bone,
   the second pin is configured to simultaneously pass through the second reposition hole, the second fixing hole, and another portion of the aligned bone,
   the third pin is configured to simultaneously pass through the third reposition hole and another portion of the aligned bone,
   the fourth pin is configured to simultaneously pass through the fourth reposition hole and another portion of the aligned bone,
   the first pin and the second pin are located on one side with respect to the osteotomy site, wherein the second pin is located closer to the osteotomy site than the first pin,
   the third pin and the fourth pin are located on the opposite side with respect to the osteotomy site, and
   the first central reposition hole axis is spaced apart at a predetermined distance from the first central fixing hole axis such that the first pin is tilted with respect to the first central fixing hole axis when the first pin passes through the first reposition hole and the first fixing hole, the second central reposition hole axis is spaced apart at a predetermined distance from the second central fixing hole axis such that the second pin is tilted with respected to the second central fixing hole axis when the second pin passes through the second reposition hole and the second fixing hole.

5. The guide module of claim 4, wherein the first central reposition hole axis is shifted toward the osteotomy site more than the first central fixing hole axis, and the second central fixing hole axis is shifted toward the osteotomy site more than the second central reposition hole axis.

* * * * *